US012350419B2

(12) United States Patent
Rentsch et al.

(10) Patent No.: US 12,350,419 B2
(45) Date of Patent: Jul. 8, 2025

(54) PORTABLE DEVICE FOR ADMINISTERING A PHYSIOLOGICALLY ACTIVE LIQUID

(71) Applicant: WERRTA GmbH Düsen- und Zerstäubungstechnik, Berlin (DE)

(72) Inventors: Rüdiger Rentsch, Berlin (DE); Mathias Etzold, Berlin (DE)

(73) Assignee: WERRTA GmbH Düsen- und Zerstäubungstechnik, Berlin (DE)

( * ) Notice: Subject to any disclaimer, the term of this patent is extended or adjusted under 35 U.S.C. 154(b) by 997 days.

(21) Appl. No.: 17/430,265

(22) PCT Filed: Feb. 13, 2020

(86) PCT No.: PCT/EP2020/053782
§ 371 (c)(1),
(2) Date: Aug. 11, 2021

(87) PCT Pub. No.: WO2020/165356
PCT Pub. Date: Aug. 20, 2020

(65) Prior Publication Data

US 2022/0160052 A1 May 26, 2022

(30) Foreign Application Priority Data

Feb. 14, 2019 (DE) ..................... 20 2019 000 718.0
Oct. 2, 2019 (DE) ..................... 20 2019 004 067.6

(51) Int. Cl.
*A61M 11/00* (2006.01)
*A24F 42/20* (2020.01)
(Continued)

(52) U.S. Cl.
CPC ........... *A61M 11/006* (2014.02); *A24F 42/20* (2020.01); *A24F 42/60* (2020.01); *A61M 11/00* (2013.01);
(Continued)

(58) Field of Classification Search
CPC ....... A24F 42/60; A24F 42/20; A61M 11/007; A61M 15/0015; A61M 2205/8281;
(Continued)

(56) References Cited

U.S. PATENT DOCUMENTS 2,406,997 A * 9/1946 Curry .................. A61M 11/002
239/338
2,434,875 A * 1/1948 Turnbull ............. B05B 11/1001
604/207
(Continued)

FOREIGN PATENT DOCUMENTS

CN 201437007 U * 4/2010 ........... A61H 35/008
DE 102005030803 A1 1/2007
(Continued)

OTHER PUBLICATIONS

English translation for DE 202017005165, machine translated by Espacenet.com, translated on Nov. 6, 2024.*
(Continued)

*Primary Examiner* — Tu A Vo
(74) *Attorney, Agent, or Firm* — Patterson + Sheridan, LLP (57) ABSTRACT

Embodiments herein describe a portable device for administering a physiologically active liquid that includes a container for holding the liquid, a pressure system for applying pressure to the liquid, an atomizer for atomizing the liquid, and an applicator for administering atomized liquid. The atomizer includes at least one nozzle through which liquid can be ejected from the container and an impact element on the nozzle outlet side that is functionally combined with the nozzle. Moreover, the atomizer is configured in such a way that, in a pressure range that can be generated with the pressurizing system, liquid emerging from the nozzle breaks up into droplets prior to striking the impact element.

25 Claims, 7 Drawing Sheets

(51) Int. Cl.
  *A24F 42/60* (2020.01)
  *A61F 9/00* (2006.01)
  *A61M 15/00* (2006.01)
  *A61M 15/08* (2006.01)
  *B05B 1/14* (2006.01)
  *B05B 1/26* (2006.01)
  *B05B 1/28* (2006.01)
  *B05B 7/00* (2006.01)
  *B05B 11/10* (2023.01)
  *B05B 14/00* (2018.01)
  *B65D 83/14* (2025.01)
  *B65D 83/62* (2006.01)
  *B65D 83/64* (2006.01)

(52) U.S. Cl.
  CPC ......... *A61M 11/007* (2014.02); *A61M 11/008* (2014.02); *A61M 15/0001* (2014.02); *A61M 15/0015* (2014.02); *A61M 15/08* (2013.01); *B05B 1/14* (2013.01); *B05B 1/262* (2013.01); *B05B 1/28* (2013.01); *B05B 7/0012* (2013.01); *B65D 83/753* (2013.01); *B65D 83/754* (2013.01); *A61F 9/0008* (2013.01); *A61M 11/003* (2014.02); *A61M 2205/8281* (2013.01); *A61M 2207/00* (2013.01); *B05B 11/1052* (2023.01); *B05B 14/00* (2018.02); *B65D 83/62* (2013.01); *B65D 83/64* (2013.01)

(58) Field of Classification Search
  CPC ........ A61M 11/008; A61M 2205/3334; A61M 11/001; A61M 11/02; A61M 11/003; A61M 15/009; A61M 15/06; A61M 16/0808; A61M 2205/8225; A61M 2207/00; A61M 11/00; A61M 11/006; A61M 11/08; A61M 15/00; A61M 15/0001; A61M 15/08; B05B 1/262; B05B 11/1052; B05B 1/14; B05B 7/0012; B05B 1/28; B05B 14/00; A61F 9/0008; B65D 83/753; B65D 83/754; B65D 83/62; B65D 83/64; B65D 83/205
  See application file for complete search history.

(56) References Cited

U.S. PATENT DOCUMENTS

| | | | | | |
|---|---|---|---|---|---|
| 2,622,593 | A * | 12/1952 | Peirano | ............... | A61M 11/065 122/489 |
| 2,906,463 | A * | 9/1959 | Curry | ............... | B05B 11/06 261/78.2 |
| 3,069,097 | A * | 12/1962 | Cheney | ............... | A61M 11/06 239/338 |
| 3,302,374 | A * | 2/1967 | Szekely | ............... | A61M 11/00 261/78.2 |
| 3,522,806 | A * | 8/1970 | Szekely | ............... | A61M 11/06 239/338 |
| 3,838,686 | A * | 10/1974 | Szekely | ............... | B05B 7/0012 239/338 |
| 4,368,850 | A | 1/1983 | Szekely | | |
| 4,940,051 | A * | 7/1990 | Lankinen | ............... | A61M 15/0015 128/200.23 |
| 5,048,729 | A | 9/1991 | Pritchard | | |
| 5,355,873 | A * | 10/1994 | Del Bon | ............... | B05B 9/0883 482/13 |
| 5,490,630 | A * | 2/1996 | Hecker | ............... | A61M 15/00 239/338 |
| 6,062,212 | A * | 5/2000 | Davison | ............... | B05B 17/0646 128/200.14 |
| 9,624,021 | B2 * | 4/2017 | Bodet | ............... | B05C 17/00559 |
| 10,106,311 | B2 * | 10/2018 | Mekata | ............... | B65D 83/64 |
| 2003/0178507 | A1 * | 9/2003 | Maria Rijn Van | ..... | B01D 61/18 239/337 |
| 2005/0001076 | A1 | 1/2005 | Eicher et al. | | |
| 2005/0103330 | A1 * | 5/2005 | Anderson | ............... | B23H 9/14 128/200.23 |
| 2006/0169800 | A1 * | 8/2006 | Rosell | ............... | A61M 15/0003 239/418 |
| 2008/0048054 | A1 * | 2/2008 | Peters | ............... | B05B 1/26 29/890.07 |
| 2008/0272144 | A1 * | 11/2008 | Bonney | ............... | B05B 11/109 222/71 |
| 2011/0290244 | A1 * | 12/2011 | Schennum | ............... | A24F 42/60 128/200.23 |
| 2013/0199521 | A1 * | 8/2013 | Hausmann | ............... | A61M 11/007 128/200.23 |
| 2013/0319404 | A1 * | 12/2013 | Feriani | ............... | A61M 11/005 239/102.1 |
| 2015/0122836 | A1 * | 5/2015 | Bodet | ............... | B05B 11/028 222/136 |
| 2015/0174595 | A1 | 6/2015 | Young et al. | | |
| 2017/0143915 | A1 * | 5/2017 | Strange | ............... | A61M 11/002 |
| 2018/0117267 | A1 | 5/2018 | Nadler | | |
| 2018/0214894 | A1 | 8/2018 | Meshberg | | |
| 2020/0330704 | A1 | 10/2020 | Rentsch | | |

FOREIGN PATENT DOCUMENTS

| | | | | |
|---|---|---|---|---|
| DE | 102014207657 | B3 | 7/2015 | |
| DE | 202015009408 | U1 * | 8/2017 | |
| DE | 202017002851 | U1 * | 8/2017 | |
| DE | 202017005165 | U1 * | 11/2017 | .......... A61M 11/003 |
| EP | 0119511 | A2 * | 9/1984 | |
| EP | 1386670 | A2 | 2/2004 | |
| EP | 1493492 | A1 | 1/2005 | |
| EP | 3315207 | A1 | 5/2018 | |
| EP | 3351172 | A1 | 7/2018 | |
| GB | 2120958 | B * | 7/1985 | ............ B05B 1/265 |
| JP | S4942799 | U | 4/1974 | |
| JP | 2015159991 | A | 9/2015 | |
| RU | 2495726 | C2 | 10/2013 | |
| WO | WO-9219383 | A1 * | 11/1992 | ............ B05B 1/262 |
| WO | 2015173569 | A1 | 11/2015 | |
| WO | 2016184761 | A1 | 11/2016 | |
| WO | 2017167610 | A1 | 10/2017 | |
| WO | 2020165356 | A1 | 8/2020 | |

OTHER PUBLICATIONS

English translation for DE 202015009408, machine translated by Espacenet.com, translated on Nov. 6, 2024.*
English translation for DE 202017002851, machine translated by Espacenet.com, translated on Nov. 7, 2024.*
English translation for CN201437007, machine translated by Espacenet.com, translated on Nov. 7, 2024.*
English translation for EP 0119511, machine translated by Search clarivate analytics, translated on Nov. 8, 2024.*
Austrian Patent Office, Communication-Search Report for Application 112/2019 dated Jun. 2, 2023.
S. P.. Lin et al., "Drop and Spray Formation from a Liquid Jet," Annual Review of Fluid Mechanics, vol. 30. No. 1, Jan. 1, 1998, pp. 85-105.
European Patent Office, Communication gema.B Article 94(3) EPO for Application 20 708 038.3-1122 dated Jan. 19, 2023.
Federal Institue of Industrial Property, Russian Office Action for Application No. 2021126790/14 dated Jun. 3, 2023.
Hermans, M. et al.: Selective, Laser-Induced Etching of Fused Silica at High Scan-Speeds Using KOH, JLMN—Journal of Laser Micro/Nanoengineering vol. 9, No. 2, 2014.
Etzold, M. et al.: A novel spray generator for low-energy oil burners, International Journal of Spray and Combustion Dynamics 2016, 53-64.
International Search Report for Application No. PCT/EP2020/053782 dated Apr. 6, 2020.

(56) References Cited

OTHER PUBLICATIONS

Japanese Patent Office, Notice of Reasons for Refusal for Application 2021-547592 dated Jul. 12, 2023.

* cited by examiner

PORTABLE DEVICE FOR ADMINISTERING A PHYSIOLOGICALLY ACTIVE LIQUID

The present invention relates to a portable device for administering a physiologically active liquid, in particular as an aerosol.

Inhalation devices for administering aerosols are known from the prior art, for example medical inhalers or devices for smoking cessation or as alternatives to tobacco products, such as e-cigarettes.

Inhalers are well known as devices which atomize a liquid and enable the user to inhale the aerosol produced by atomization. Fluids for inhalation used therein mostly consist of water to which one or more medicinal substances may be added.

Conventional inhalers have a reservoir for the inhalation liquid, an atomizer through which the inhalation liquid is atomized, and an applicator which allows the aerosol produced by atomization to be supplied to the airways of the user in a more or less targeted manner. For example, the applicator can be a mask to be placed over the nose and/or mouth or a tube that can be enclosed at one end by the mouth, usually with a round or oval cross-section.

An essential part of the atomizer is usually a nozzle arrangement having one or more nozzle openings from which the inhalation liquid emerges, forming droplets and, together with the surrounding gas, usually air, an aerosol. In addition to the energy that is required to move the inhalation liquid through the nozzle arrangement, the surface energy must also be brought in for the surfaces of the droplets to be formed. The smaller the resulting droplets, the greater the total surface area of the aerosol and, correspondingly, the amount of energy required.

Inhalers can be operated with a compressed propellant such as compressed air. Technically more complex inhalers often work with energy sources other than or in addition to compressed propellants, for example electromechanically or by means of ultrasonic atomization. Due to the technical complexity and the associated costs, the range of applications for such inhalers is limited. In particular, they cannot simply be plugged in so that they are immediately available when needed, for example during exercise, when traveling, or in normal everyday life.

Inhalers operating on the Venturi principle use a gas stream that entrains liquid in a dual flow nozzle. By striking an impact plate, the liquid of the two-substance stream is further atomized. The operation of such inhalers requires high gas throughputs and is therefore not suitable for portable use with long inhalation times.

A transportable inhaler is known from WO 2016/184761 A1, said transportable inhaler being equipped with a liquid reservoir for inhalation liquid, which is pressurized by the application of propellant gas, compressed air or by a pre-tensioned spring device. In this case, the liquid reservoir can have a defined volume, such that air flows in according to the liquid discharge, or it can be unventilated and have a volume that is variable via a bag or a drag piston. The storage of propellant gas in the liquid reservoir is described in WO 2016/184761 A1 as a possible variant, as is a manual pumping device. No information is given on the level of the pressures used or on the dimensioning of the volumes of liquid storage and overpressure air storage. The liquid emerges through a nozzle plate which has a large number of parallel nozzle openings. This is intended to achieve a droplet size distribution that is as monodisperse as possible.

Published patent DE 10 2014 207 657 B3 discloses a method for generating a liquid spray in which an impact element is provided with an elevation on which a continuous liquid jet and a droplet jet strike alternately. The droplet jet is generated by introducing vibrations using a piezo element; if no vibrations are introduced, the result is a continuous jet.

The size and size distribution of the droplets that are produced during atomization in the inhaler are of great importance. This is because, depending on their size, droplets of an inhaled aerosol may only reach the upper airways or the bronchi; aerosol droplets are only respirable below a droplet diameter of approximately 10 µm; depending on the target disposition, a droplet size of between 2 and 5 µm can be considered ideal.

It has been shown that conventional inhalers can only generate sufficiently small droplets over a sufficiently long period of time if the inhalers are either operated with a stationary compressed air source or are designed as electrically operated units. In particular, conventional spray cans, to which a standard filling pressure of 13.2 bar (1.32 MPa) is applied, have so far hardly been suitable for use as an inhaler, especially when the active ingredients in the inhalation liquid are to reach the lungs directly.

In the case of inhalation devices for administering small doses of nicotine, commonly known as e-cigarettes, there is usually no purely mechanical discharge of the nicotine-containing liquid, rather the liquid is heated such that condensed droplets of vapor are inhaled. When heated, however, undesirable chemical processes are initiated, which can result in undesirable, even toxic, compounds in the droplet condensate.

Against this background, it is the object of the present invention to create a portable device for administering a physiologically active liquid, said portable device being able to be used in a mobile manner and supplying sufficiently small aerosol droplets during its entire duration of application.

According to one aspect of the present invention, a portable device for administering a physiologically active liquid is provided, said portable device comprising a container for holding the liquid, pressurizing means for applying pressure to the liquid, an atomizer for atomizing the liquid and an applicator for administering atomized liquid. The atomizer has at least one nozzle through which liquid can be ejected from the container, and an impact element (for example an impact plate) on the nozzle outlet side, said impact element being functionally combined with the nozzle and configured in such a way that, in a pressure range that can be generated with the pressurizing means, liquid emerging from the nozzle breaks up into droplets prior to striking the impact element.

The liquid jet emerging from the nozzle is thus advantageously subject to free break-up into droplets, which then impinge on the impact plate and are thus atomized into smaller droplets. A targeted vibratory excitation of the jet, a jet interruption or modulation of the liquid ejection through the nozzle is therefore not necessary according to the invention.

Such a design can be carried out empirically using simple design experiments. A person skilled in the art can orientate himself on the following relationship $$Z = D \ln \frac{D}{2C} \sqrt{We} \, [1 + 3 \cdot Oh]$$

for the jet break-up length Z, in which $$We = \frac{\rho U^2 D}{\sigma}$$

denotes the Weber number and $$Oh = \frac{\eta}{\sqrt{D\sigma\rho}}$$

denotes the Ohnesorge number
with Z Jet break-up distance in m
  D Narrowest nozzle diameter in m
  C Initial perturbation of the jet break-up in m
  ρ Density of the physiologically active liquid in kg/m³
  σ Surface tension of the physiologically active liquid in N/m
  η Viscosity of the physiologically active fluid in Pa s
  U Outlet velocity of the liquid jet from the nozzle The initial perturbation of the jet break-up C is usually unknown, but it has been shown for the present invention that a value of the dimensionless factor $$\ln\frac{D}{2C}$$

can usually be assumed to amount between 10 and 15, mostly from 12 to 13.

In the case of impact atomization of droplets formed by free jet break-up in a device according to the invention are, according to experimental values, for example With a nozzle diameter of D=15 μm and pressures from 15 to 25 bar:
  $D_{v90} \approx 10$ μm
  $D_{v50} \approx 5$ to 7 μm
  $D_{v10} \approx 3$ μm With a nozzle diameter of D=10 μm and pressures of approx. 25 bar:
  $D_{v90} \approx 4$ μm
  $D_{v50} \approx 1$ to 2 μm
  $D_{v10} \approx 1$ μm The diameter specifications in the above examples are to be understood as follows:
  $D_{v10}$ 10% of the liquid volume of the aerosol consists of droplets smaller than $D_{v10}$
  $D_{v50}$ 50% of the liquid volume of the aerosol consists of droplets smaller than $D_{v50}$
  $D_{v90}$ 90% of the liquid volume of the aerosol consists of droplets smaller than $D_{v90}$ According to a particularly advantageous development, the device has a collection device for collecting excess liquid dripping or running from the impact element. The use of an impact element according to the invention always leads to a certain proportion of unused liquid dripping from the impact element. For the handling of a portable inhaler or another portable device for applying an aerosol, it is of great advantage if the user is not impaired by liquid dripping out of the device in an uncontrolled manner, but rather said liquid is held back in a controlled manner.

According to an advantageous embodiment, the collection device and the applicator can be integrated jointly into one component.

According to a further advantageous embodiment, the collection device and the impact element can be integrated jointly into one component.

According to a further advantageous embodiment, the collection device can comprise a reservoir. Advantageously, the reservoir can comprise a replaceable or non-replaceable integrated absorbent material, for example a fleece, sponge, zeolite or similar.

According to a further advantageous embodiment, the device can be configured to supply at least part of the excess liquid from the collection device to the atomizer for re-atomization. Such a recirculation allows a larger proportion of the liquid provided in the container to be used and the maximum possible duration of use with one container filling can be increased.

According to a particularly advantageous development, the container can be a pressure tank which has a gas compartment filled with compressed gas as pressurizing means and a liquid compartment filled with liquid, wherein the atomizer comprises a valve such that liquid can be ejected from the liquid compartment through the nozzle when the valve is open, in that the gas compartment increases proportionally to the quantity of liquid ejected by the expansion of the gas and the liquid compartment thereby decreases by the volume of the liquid ejected, such that a maximum possible change in volume of the gas compartment or liquid compartment compared to a specific initial filling state of the gas compartment or liquid compartment defines a maximum ejection quantity of liquid for the specific initial filling state.

According to an advantageous embodiment, the pressure of the compressed gas in the initial filling state can be so high that the pressure in the liquid compartment does not fall below 13 bar (1.3 MPa) before the maximum ejection quantity of inhalation liquid has been ejected. According to an advantageous embodiment, the pressure of the compressed gas in the initial filling state is at least 18 bar (1.8 MPa), preferably at least 20 bar (2 MPa), particularly preferably at least 25 bar (2.5 MPa).

In a manner surprising to a person skilled in the art, even with embodiments in which pressures in the liquid compartment fall below 13 bar (1.3 MPa) during the ejection process or below 13 bar (1.3 MPa) during the entire ejection process, it is possible, through the free break-up into droplets in connection with the impact element, to maintain suitable atomization parameters for the generation of respirable droplets over the entire duration of use. As a result of the lower pressures, such embodiments place lower demands on the manufacture of the pressure tank and valve and can therefore be particularly advantageous. An embodiment in which the initial pressure of the liquid in the container is 13 bar (1.3 MPa) or below can also be regarded as particularly advantageous because a correspondingly lower outlet pressure can promote free break-up into drops.

For the dimensioning, the residual pressure remaining after the maximum ejection quantity of inhalation liquid has been ejected can be determined by means of the general gas law. According to the invention, the volumes of the gas compartment and the liquid compartment are coupled to one another (for example via a movable piston that separates the two compartments from one another) in such a way that the maximum (initial) volume of the liquid compartment and thus a minimum (initial) volume $V_1$ of the gas compartment are specified by the maximum filling quantity of the liquid compartment with physiologically active liquid. The minimum (final) volume of the liquid compartment after the corresponding maximum ejection quantity of inhalation liquid has been ejected and, through the coupling, the maximum (final) volume $V_2$ of the gas compartment is also specified (for example by means of a stopper). The final pressure $p_2$ in the gas compartment corresponds to the minimum pressure in the liquid compartment until the maximum ejection quantity of inhalation liquid is ejected and the difference between the final and initial volume of the gas compartment without transmission of the difference between the initial and final volume of the liquid compartment.

According to the ideal gas law $$p_1 \cdot V_1 = p_2 \cdot V_2$$

the initial pressure of the compressed gas is to be determined according to the relationship $$p_1 = p_2 \cdot V_2 / (V_2 - V_{Fmax})$$

wherein $V_{Fmax}$ is the maximally ejectable volume of liquid.

For dimensioning, the lowest possible pressure is selected for $p_2$, which provides a droplet size distribution within the desired parameters (defined e.g. via the Sauter mean diameter $d_{32}$, i.e. six times the reciprocal of the specific surface area of the droplets of the aerosol) for the intended geometry of the atomizer, which can be done, for example, using simple design experiments, and then, for the desired application quantity of inhalation liquid corresponding to $V_{Fmax}$, it can be determined how high the filling pressure has to be at the available initial volume of the gas compartment in accordance with the above relationship.

Conversely, the required final volume of the gas compartment can of course also be determined on the basis of the maximum available gas filling pressure if a specific residual pressure is to be maintained. With a given application quantity (=maximum ejection volume) of 150 ml of liquid and a minimum pressure in the liquid compartment of 1.3 MPa (immediately before the last droplet is ejected) as well as a maximum available filling pressure of 3 MPa for the gas compartment, for example, the final volume of the gas compartment would have to be measured as $$V_2 = 150\text{ ml}/(1 - 1.3\text{ MPa}/3\text{ MPa}) = 264.7\text{ ml}$$

after converting the above relationship.

According to an advantageous development, the valve can be designed as a regulating valve, by means of which the volume flow of liquid ejected can be regulated. Here, a person skilled in the art can resort to valve designs known per se from the prior art.

According to a particularly advantageous development, the device can have a transmission which increases the pressure in the liquid compartment compared to the pressure in the gas compartment. The design relationship explained above must then be adapted accordingly, although the initial and final volumes as well as the initial and final pressures of the gas compartment can still be dimensioned on the basis of the general gas law. However, a proportionality factor between the volume change in the gas compartment and the volume change in the liquid compartment and a transmission ratio between the pressures in the gas compartment and in the liquid compartment must then be taken into account.

If the transmission is advantageously implemented with the aid of a gas piston delimiting the gas compartment on one side with a gas compartment piston surface on the gas compartment side and a liquid piston delimiting the liquid compartment on one side with a liquid compartment piston surface on the liquid-compartment side, wherein the surface area $A_F$ of the liquid compartment piston surface is smaller than the surface area $A_G$ of the gas compartment piston surface, then a transmission ratio k between the pressure in the liquid compartment and the pressure in the gas compartment of $$k = A_G : A_F$$

and, as a change in volume in the gas compartment, k times the respective quantity of inhalation liquid ejected will result.

For the design of the gas compartment, $p_2 \geq 1.3$ MPa/k and $$p_1 = p_2 \cdot V_2 / (V_2 - k \cdot V_{Fmax})$$

wherein (as above) $p_2$:=final pressure in the gas compartment; $p_1$:=initial filling pressure in the gas compartment; $V_{Fmax}$:=maximally ejectable quantity of inhalation liquid; $V_2$:=final volume of the gas compartment.

The above applies when the paths of the gas and liquid pistons are coupled in such a way that a specific displacement of one piston causes an equal displacement of the other piston. Pistons can of course also be coupled in other ways via lever mechanisms, gears or similar. Transmission mechanisms with spindle drives and similar can also be implemented.

According to a preferred embodiment, the surface area of the liquid compartment piston surface is less than or equal to half the surface area of the gas compartment piston surface, such that a transmission ratio between the pressure in the liquid compartment and the pressure in the gas compartment of k≥2 results when the paths of the gas and liquid pistons are coupled in such a way that a specific displacement of one piston causes an equal displacement of the other piston.

The transmission between the gas compartment and the liquid compartment offers the advantage that higher liquid pressures can be generated with lower gas pressures, such that the pressure tank only has to be designed for lower gas pressures, and safety can be increased. This is because high liquid pressures are already reduced with minimal expansion (e.g. due to a leak), whereas high gas pressures can pose a safety risk and even risk of explosion. Such a transmission can advantageously be implemented not only for devices for administering physiologically active liquids, in particular inhalers, but also for spray cans of all kinds, wherein the liquid compartment can also be replaced by a multi-component compartment. Accordingly, a spray can, in particular also a spray can with a spray head of the type known from DE 20 2017 002 851 U1, or DE 20 2017 005 165 U1 or EP 3315207 A1, can advantageously be provided, said spray can having a pressure tank for receiving a spray liquid or a multi-component mixture to be sprayed and compressed gas and an atomizer for atomizing the spray liquid or the multi-component mixture to be sprayed, wherein the pressure tank has a gas compartment filled with the compressed gas and a liquid compartment filled with the spray liquid or a multi-component compartment filled with the multi-component mixture, wherein the atomizer has a valve and at least one nozzle through which spray liquid or multi-component mixture can be ejected from the liquid compartment when the valve is open, in that the gas compartment increases by expansion of the gas and the liquid compartment or multi-component compartment thereby decreases by the volume of the ejected spray liquid or of the ejected multi-component mixture, wherein a transmission is provided which increases the pressure in the liquid compartment or multi-component compartment compared to the pressure in the gas compartment.

An atomizer having at least one nozzle through which liquid can be ejected from the container, and an impact element on the nozzle outlet side, said impact element being functionally combined with the nozzle and designed in such a way that, in a pressure range that can be generated with the pressurizing means, liquid emerging from the nozzle breaks up intro droplets prior to striking the impact element, features particularly good atomization even in lower pressure ranges. If the above design criterion is used, according to which the pressure of the compressed gas in the initial filling state is so high that the pressure in the liquid compartment does not fall below 13 bar (1.3 MPa) before the maximum ejection quantity of inhalation liquid has been ejected, alternative atomizers can also be particularly advantageous. Accordingly, an inhaler can advantageously be provided in general terms, said inhaler having a pressure tank for receiving inhalation liquid and compressed gas, an atomizer for atomizing the inhalation liquid and an applicator for administering the atomized inhalation liquid, wherein the pressure tank has a gas compartment filled with the compressed gas and a liquid compartment filled with the inhalation liquid, the atomizer has a valve and at least one nozzle, through which inhalation liquid can be ejected from the liquid compartment when the valve is open, in that the gas compartment increases proportionally to the quantity of inhalation liquid ejected by the expansion of the gas and the liquid compartment thereby decreases by the volume of the inhalation liquid ejected, such that a maximum possible change in volume of the gas compartment or liquid compartment compared to a specific initial filling state of the gas compartment or liquid compartment defines a maximum ejection quantity of inhalation liquid for the specific initial filling state, wherein the pressure of the compressed gas in the initial filling state is so high that the pressure in the liquid compartment does not fall below 13 bar (1.3 MPa) before the maximum ejection quantity of inhalation liquid has been ejected. In a way that is surprising to a person skilled in the art, it is possible to obtain suitable atomization parameters for the generation of respirable droplets over the entire duration of use by suitably matching the filling volumes of the gas compartment and the liquid compartment and the initial filling pressure of the gas compartment.

According to a preferred embodiment of the inhaler having an alternative atomizer, the at least one nozzle is designed as a plurality of Rayleigh nozzle holes, for example round holes in a nozzle plate.

It has been found that with nozzle holes of the same size for pressures above 1.3 MPa and (smallest) hole diameters in the single-digit micrometer range, almost monodisperse droplets with an average diameter of approximately 1.89 times the hole diameter can be produced.

Correspondingly, the smallest diameter of each of the Rayleigh nozzle holes can advantageously be 6 μm or less, preferably 3 μm or less, particularly preferably between 1 μm and 3 μm.

In the present application, a smallest diameter of a nozzle or nozzle opening is understood to mean the smallest possible distance between the two points of intersection of a line that orthogonally intersects the center axis of the flow-through channel (outlet channel) forming the nozzle opening with the edge of the respective outlet channel. If, for example, an outlet channel is essentially cylindrical but not drilled orthogonally to a flat surface which forms the edge of the outlet opening, the result is an elliptical outlet opening whose shorter main axis corresponds to the smallest diameter of the outlet channel.

In principle, the number of nozzle holes is advantageously measured according to the desired liquid throughput if the hole diameter is fixed on the basis of the desired droplet size.

According to a preferred embodiment of the inhaler having an alternative atomizer, at least 20 Rayleigh nozzle holes are provided.

According to a further advantageous enhancement of the inhaler having an alternative atomizer, more than one nozzle can be provided, wherein the nozzles can be excluded from the supply of inhalation liquid individually or in groups. In this way, the volume flow of ejected inhalation liquid can be controlled by having more or fewer nozzles involved in atomization. If different nozzles, for example nozzles with different outlet diameters, are used, atomization parameters such as droplet size or size distribution can be configured by selectively selecting certain nozzles or groups of nozzles. Different technical implementations are advantageously possible here, for example perforated disks which can be displaced against one another with different overlap of the holes, depending on the position, separate valves for separate nozzles or nozzle groups, etc. A nozzle plate having a plurality of nozzle openings can also be covered in different proportions by a valve plate, such that, for example, only larger, only smaller or larger and smaller nozzle openings can flow onto said valve plate.

According to a further advantageous embodiment of the inhaler having an alternative atomizer, the nozzle is designed as at least one multi-jet nozzle arrangement, in particular with at least two outlet channels, which are arranged in such a way that spray jets emerging from at least two of the outlet channels meet centrally at a respective point of impact that is spaced from the outlet openings. Advantageous designs for such multi-jet nozzles can essentially be designed as disclosed in EP 3351172 A1 or in a similar manner.

As a result of the pressure ratios defined above (high residual pressure), embodiments of the inhaler having an alternative atomizer in which the smallest diameter (diameter of the outlet channel as explained above) of the at least one nozzle is 50 μm or less, preferably 20 μm or less, particularly preferably 10 μm or less, can be implemented particularly advantageously. In multi-jet nozzles of the type mentioned, droplet sizes can be reduced by increasing the pressure and reducing the diameter of the outlet channels.

According to a further advantageous embodiment of the inhaler having an alternative atomizer, the nozzle is designed as at least one hollow-cone nozzle. Advantageous designs for multi-jet nozzles of this type can be designed essentially as disclosed in DE 20 2017 005 165 U1 or similar (i.e. also with deviations such as, in particular, an essentially axial liquid inlet).

As a result of the pressure ratios defined above (high residual pressure), embodiments of the inhaler having an alternative atomizer in which the smallest diameter of the outlet of the hollow-cone nozzle (as explained above) is 100 μm or less, preferably 50 μm or less, particularly preferably 20 μm or less, can be implemented particularly advantageously. In the case of hollow-cone nozzles with tangential liquid inlet, the pressure criterion according to the invention ensures that undesired so-called tulip formation in the nozzle body is avoided.

As an alternative to a gas compartment filled with compressed gas, the portable device according to the invention can advantageously use a hand pump, in particular a battery-operated electric pump or a spring system, as is known per se from the prior art, as pressurizing means. With such an alternative pressurizing means, the device can be configured particularly advantageously in such a way that at least part of the excess liquid from the collection device can be supplied to the atomizer for re-atomization. All that needs to be provided for this configuration is a return flow channel, preferably with a screen or filter device, via which excess liquid that has dripped is supplied to the pump, for example.

In the present invention, as in the case of the inhaler having an alternative atomizer, the nozzle can advantageously be manufactured, as is known per se from the prior art, lithographically, by electroerosion or by means of sintering in ceramic or plastics. In the lithographic process, fine channels are etched out of a silicon nozzle body. Such manufacturing processes are known in connection with atomizer pumps or associated spray heads, for example from EP 1493492 A1 and EP 1386670 A2.

According to a particularly advantageous enhancement of the invention as well as of the inhaler having an alternative atomizer, the at least one nozzle can be manufactured by means of laser action, wherein a nozzle material, preferably quartz glass or another suitable glass material, is preferably locally exposed to laser action to form the nozzle, and the nozzle material exposed to the laser action is subsequently etched away. Quartz glass exposed to laser action can be etched away using hydrofluoric acid (HF) or preferably potassium hydroxide (KOH). Quartz glass can also be appropriately doped to improve laser machinability. Such a manufacturing process is known per se under the designation SLE (selective laser-induced etching) and is disclosed in Hermans, M. et al.: *Selective, Laser-Induced Etching of Fused Silica at High Scan-Speeds Using KOH*, JLMN-*Journal of Laser Micro/Nanoengineering* Vol. 9, No. 2, 2014. Manufacturing machines that can be used to manufacture according to the SLE process are commercially available under the name LightFab Microscanner.

According to an advantageous embodiment of the invention, the device is an inhalation device, the liquid is an inhalation liquid, and the applicator has a mouthpiece or a mouth and/or nose mask.

For smoking cessation or as an alternative to tobacco products, the applicator can have a mouthpiece and the inhalation liquid can contain nicotine. In contrast to known e-cigarettes, atomization is preferably carried out purely mechanically without heating, such that undesirable chemical processes can be avoided.

According to a further advantageous embodiment of the invention, the device can be designed as an ophthalmic nebulization device and the applicator can have an eye mask. In this way, active ingredients in ophthalmology can advantageously be applied as an aerosol, or the problem of dry eyes can be alleviated by adding liquid as an aerosol. In principle, the application of an aerosol is much more pleasant for the user compared to the administration of conventional eye drops, since the head does not have to be tilted back and the dosage is much easier.

According to a further advantageous embodiment of the invention as well as of the inhaler having an alternative atomizer, a screen arrangement is connected upstream of the at least one nozzle on the nozzle inlet side. Otherwise, especially with small outlet channels (nozzle openings), there may be a risk that these channels will become completely or partially blocked. The screen arrangement can advantageously be designed as one piece with a nozzle body, as disclosed in DE 20 2017 002 851 U1 or similar, or a separately mounted screen body can be used.

According to a further advantageous enhancement, more than one nozzle can be provided in the device according to the invention, wherein the nozzles can be excluded from the supply of inhalation liquid individually or in groups. In this way, the volume flow of ejected inhalation liquid can be controlled by having more or fewer nozzles involved in atomization.

The invention is explained in more detail herein-below in an exemplary manner with reference to the accompanying schematic drawings. The drawings are not to scale; in particular, for reasons of clarity, the proportions of the individual dimensions to one another sometimes do not correspond to the dimensional relationships in actual technical implementations. Several preferred embodiments are described, to which the invention is not limited.

In principle, every variant of the invention described or indicated in the context of the present application can be particularly advantageous, depending on the economic, technical and possibly medical conditions in the individual case. Unless stated otherwise, or as far as technically feasible in principle, individual features of the embodiments described are interchangeable or can be combined with one another as well as with features known per se from the prior art.

In the drawings

Corresponding elements are denoted by the same reference signs in the drawings.

Figure 1A:
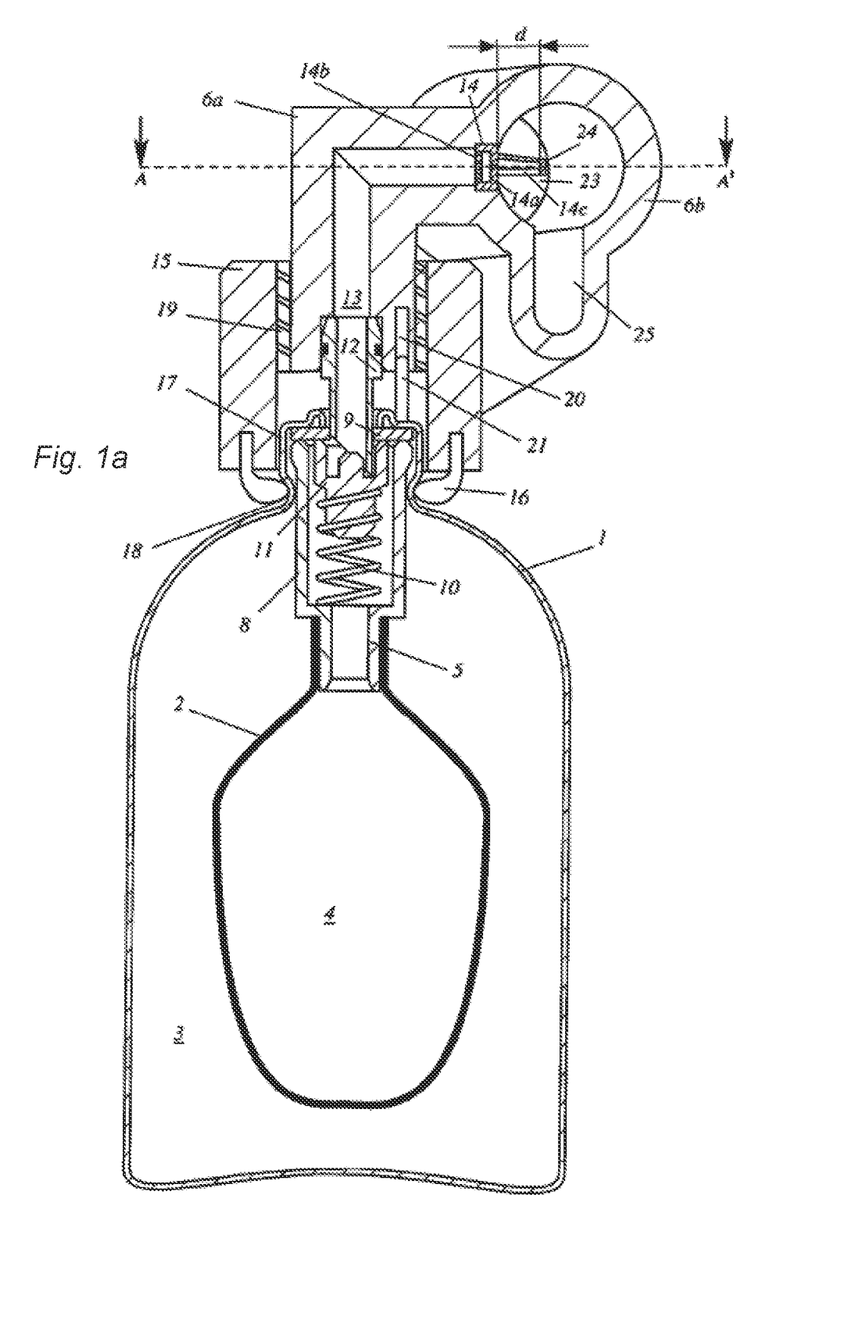
FIG. 1a is a cross-sectional representation of a device according to the invention, designed as an inhaler with a tubular applicator, having a bag-shaped liquid compartment, wherein the sectional plane of FIG. 1a is indicated in FIG. 1b as a dashed line B-B'.
Figure 1B:
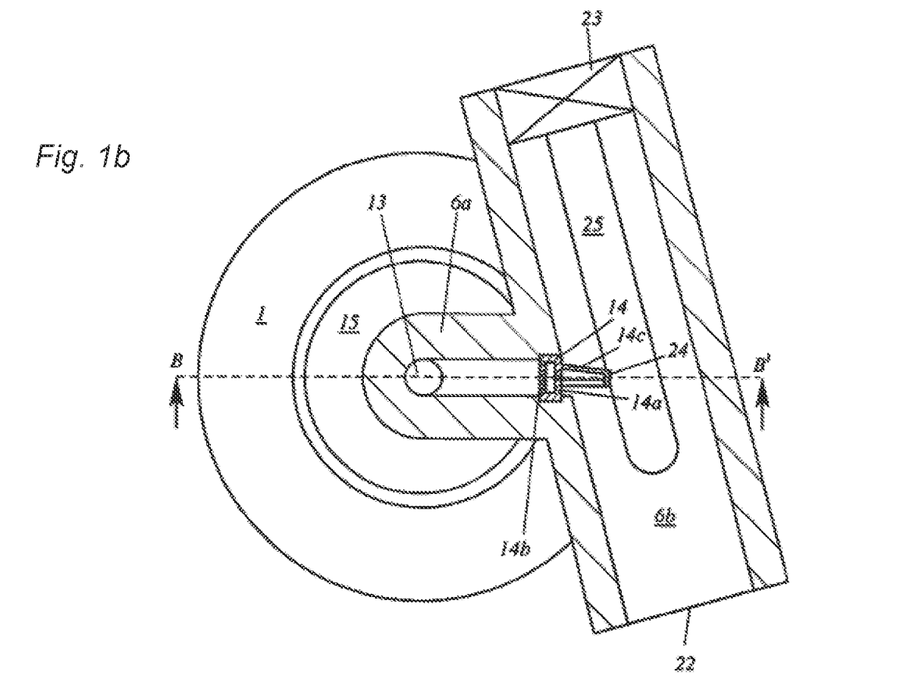
FIG. 1b is a part of a cross-sectional view of the inhaler from FIG. 1a at an angle of 90 degrees to FIG. 1a, wherein the sectional plane of FIG. 1b is indicated in FIG. 1a as a dashed line A-A'.

The inhaler shown in FIGS. 1a and 1b has a pressure tank 1 which is divided by the flexible bag 2 into the gas compartment 3 filled with compressed gas and the liquid compartment 4 containing inhalation liquid, for example brine. The bag 2 is connected, for example welded or glued, to the inlet connection 5 of the atomizer/applicator unit 6a, 6b. Instead of a bag, a separate piston can also separate the gas compartment 3 from the liquid compartment 4, for example.

The valve of the atomizer 6a is similar to conventional valves and has a valve housing 8 which is sealed by the sealing ring 9 made of an elastomer such as rubber or silicone rubber. The spring 10 inserted into the valve housing presses the sealing capsule 11 against the sealing ring 9. By compressing the hollow plunger 12 and pressure vessel 1 relative to one another, the hollow plunger 12, which is beveled at the bottom, pushes the sealing capsule 11 downward in such a way that inhalation liquid can enter the supply channel 13 of the nozzle unit 14 through the valve housing 8 and hollow plunger 12.

The atomizer/applicator unit 6a, 6b is held on the pressure tank 1 by means of a ring 15 having latching lugs 16 evenly distributed around the circumference of the ring. The latching lugs 16 engage in a circumferential constriction 18 of the pressure vessel 1 below the collar 17. The ring 15 is rotatably connected via the thread 19 to the wall of the supply channel 13 seated on the hollow plunger 12. As a result of the pin 21, which engages displaceably in the blind hole 20 of the wall of the supply channel 13 and is welded to the pressure vessel 1, the wall of the supply channel 13 and thus the applicator 6b firmly connected to the wall is non-rotatable relative to the pressure vessel 1. By rotating the ring 15, the wall of the supply channel 13 can be moved up and down together with the hollow plunger 12 in a controlled manner, thus causing the hollow plunger 12 and pressure vessel 1 to be pressed together relative to one another.

The inhalation liquid is atomized into the interior of the applicator 6b through the nozzle openings of the nozzle body 14 closing the supply channel 13. As can be seen in conjunction with FIG. 1b, the applicator 6b can be designed to be essentially tubular, such that the open end 22 of the tube is enclosed by the mouth of the user for inhalation.

By means of selective laser exposure and subsequent etching of the exposed regions (selective laser-induced etching), a nozzle plate 14a having a central outlet opening and an impact element 24 arranged opposite the outlet opening are formed in the nozzle body 14 made of quartz glass with a cylindrical basic shape, and a screen body 14b having a large number of screen openings, the diameter of which corresponds at most to the diameter of the outlet openings, in order to keep blockages away from said outlet openings.

In the present example, the impact element 24 is held by three struts 14c integrated into the nozzle body at a distance d from the outlet opening (only two of the struts 14c are visible in FIGS. 1a and 1b), wherein a different number of struts can of course be selected in the design. Using design experiments, the container pressure (preferably 13 bar or less in the liquid compartment 4), the diameter of the outlet opening in the nozzle plate 14a, and the distance d to the impact element 24 have been matched such that the liquid jet discharged from the outlet opening in the nozzle plate 14a undergoes a free drop break-up prior to striking the impact element 24.

The nozzle body 14 can be cast as a one-piece plastics cast part comprising the wall of the supply channel 13 and the applicator 6b, but said nozzle body can also be glued or clamped between two components if the wall of the supply channel 13 and the applicator 6b are not made as one piece together.

If the bag 2 has completely collapsed due to the successful ejection of the maximally ejectable quantity of inhalation liquid, the gas in the gas compartment 3, which then has its maximum volume, has a residual pressure selected according to the desired design.

FIG. 1b shows the inhaler from FIG. 1a in another sectional plane which is orthogonal to FIG. 1a. The sectional plane of FIG. 1b is indicated in FIG. 1a as a dashed line A-A', and the line of sight of the observer is indicated by arrows. Correspondingly, the sectional plane of FIG. 1a is indicated in FIG. 1b as a dashed line B-B', and the line of sight of the observer is again indicated by arrows.

Opposite the open end 22 of the applicator 6b, said open end being enclosed by the mouth of the user for inhalation, a one-way valve or gas-permeable plug 23 closes the other end of the applicator 6b.

As can be when FIGS. 1a and 1b are viewed together, the applicator has a groove 25 on its lower face which deepens in the direction of the plug 23 and flattens out in the direction of the open end 22. The groove 25 is used as a collection reservoir for liquid dripping from the impact element 24 and is closed on the side of the plug 23.

Figure 2:
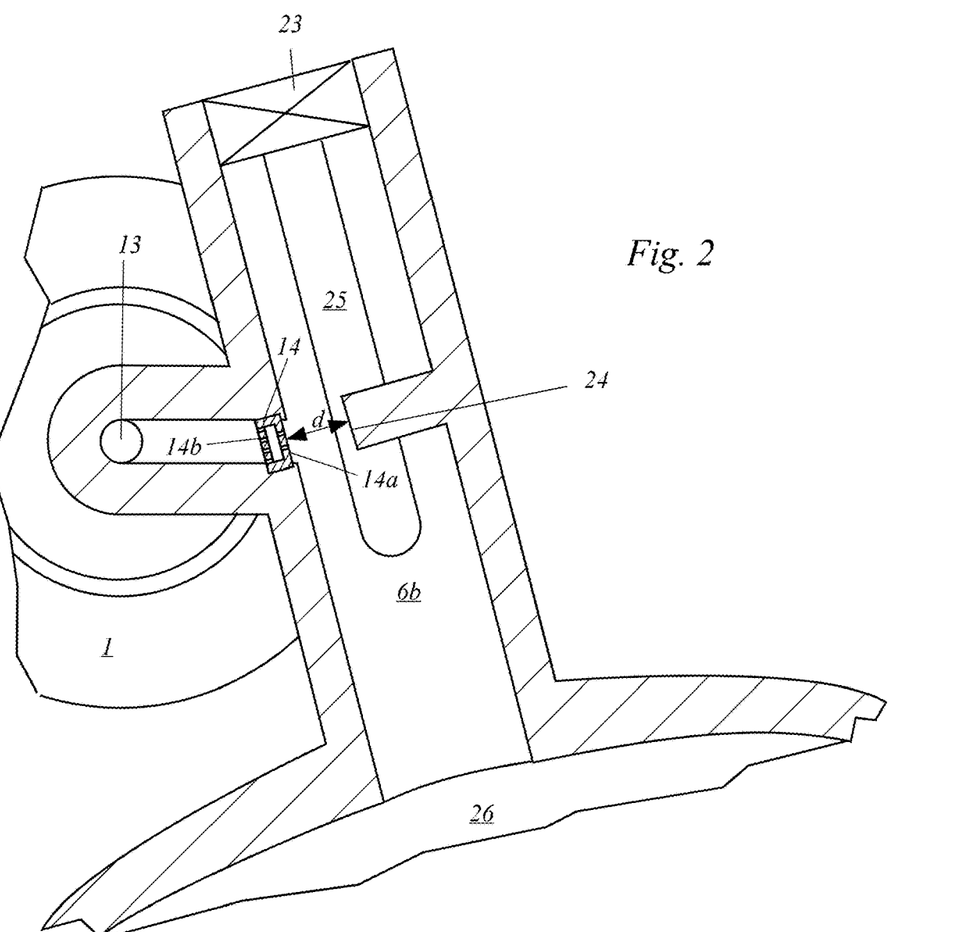
FIG. 2 is a detailed cross-sectional view similar to FIG. 1b, but the applicator of the inhaler is designed in the form of a mask.
Figure 3A:
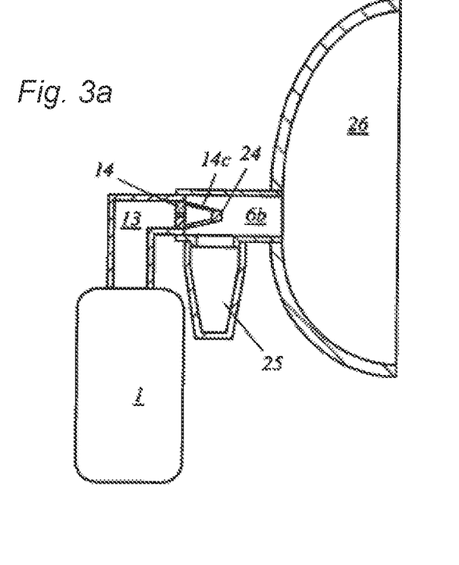
FIG. 3a shows the schematic structure of a device according to the invention, in which the impact element and nozzle are made as one piece as a common component, and the collection reservoir and an inhalation mask are each removable.
Figure 3B:
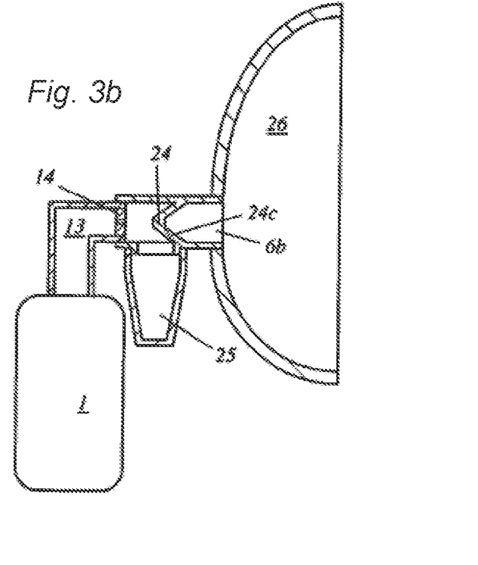
FIG. 3b shows a schematic structure similar to FIG. 3a, wherein the impact element and collection reservoir are made as one piece as a common component separate from that of the nozzle, and the inhalation mask is removable.

FIG. 2 shows, in a broken perspective view, an inhaler similar to FIG. 1b, but with an applicator 6b designed as a mask 26 at its free end. The mask 26 (shown in a broken perspective view) can be placed over the mouth and nose of the user for inhalation and is preferably wholly or partially made of a flexible plastics or silicone material. A groove 25, which is recessed in the direction of air-permeable plug 23, is again provided as a collection reservoir for unused inhalation liquid.

In contrast to FIGS. 1*a* and 1*b*, the impact element 24 is not formed as one piece with the nozzle body 14 but is integrated into the wall of the applicator 6*b*. Furthermore, the nozzle body 14 contains more than one, for example two, as shown, outlet openings. The number of outlet openings is an additional parameter that can be used to adjust the pressure loss and fluid flow rate.

Different arrangement variants of a device according to the invention constructed similarly to FIG. 2 are shown in FIGS. 3*a*, 3*b*, 4*a* and 4*b*.

In FIG. 3*a*, the impact element 24 is again integrated into the nozzle body 14. The inhalation mask 26 (mouth and nose mask) is attached, or screwed, glued or welded, to the applicator tube 6*b*. The collection reservoir 25 arranged below the impact element 24 is detachably connected (for example by a plug, screw or bayonet connection) or permanently connected (for example by welding or gluing) to the applicator tube 6*b*. Above all, if the applicator is to be designed to be reusable, a detachable connection between the applicator tube 6*b* and the collection reservoir 25 can be advantageous.

The embodiment in FIG. 3*b* corresponds to the embodiment from FIG. 3*a*, but the impact element 24 is not integrated into the nozzle body 14 but rather into the applicator tube 6*b* by means of several struts 24*c*.

In the device in FIG. 4a, an eye mask 27 and the collection reservoir 25 are integrated into one piece with the applicator tube 6b as a common component. As in FIG. 3a, the nozzle body 14 has a plurality of struts 14c which hold the impact element 24.

Figure 4A:
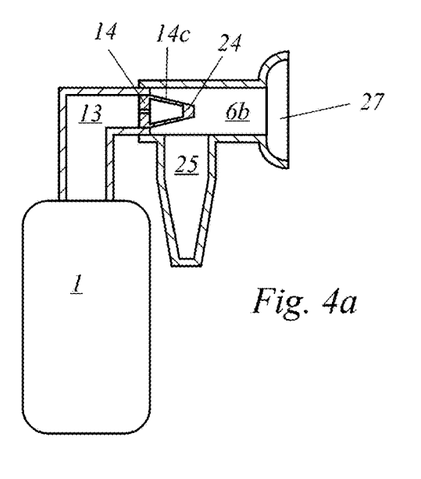
FIG. 4a shows the schematic structure of a device according to the invention similar to FIG. 3a, in which the impact element and nozzle are made as one piece as a common component, and the collection reservoir and an eye mask are also made as one piece as a common component.
Figure 4B:
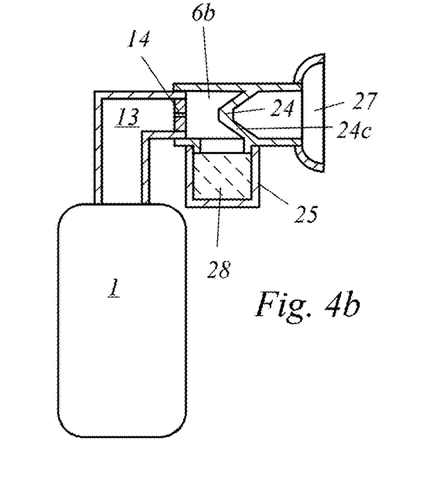
FIG. 4b shows a schematic structure similar to FIG. 4a, wherein the impact element and eye mask are combined as a common component separate from the nozzle, and the collection reservoir contains a sponge.

The device in FIG. 4b differs from the device from FIG. 4a in that the impact element 24 is not integrated into the nozzle body 14 but rather into the applicator tube 6b by means of several struts 24c. The removable collection reservoir 25 contains a sponge 28. The sponge 28 offers the advantage that excess liquid remains securely in the collection reservoir, even if the device is held at an angle or is shaken. Another absorbent material, for example a fleece, woven material, cotton ball, particle collective, etc. can also serve the function of the sponge.

The connection between the wall of the supply channel 13 to the nozzle 14 and the applicator tube 6b can be fixed or detachable in FIG. 3a-4b.

Figure 5:
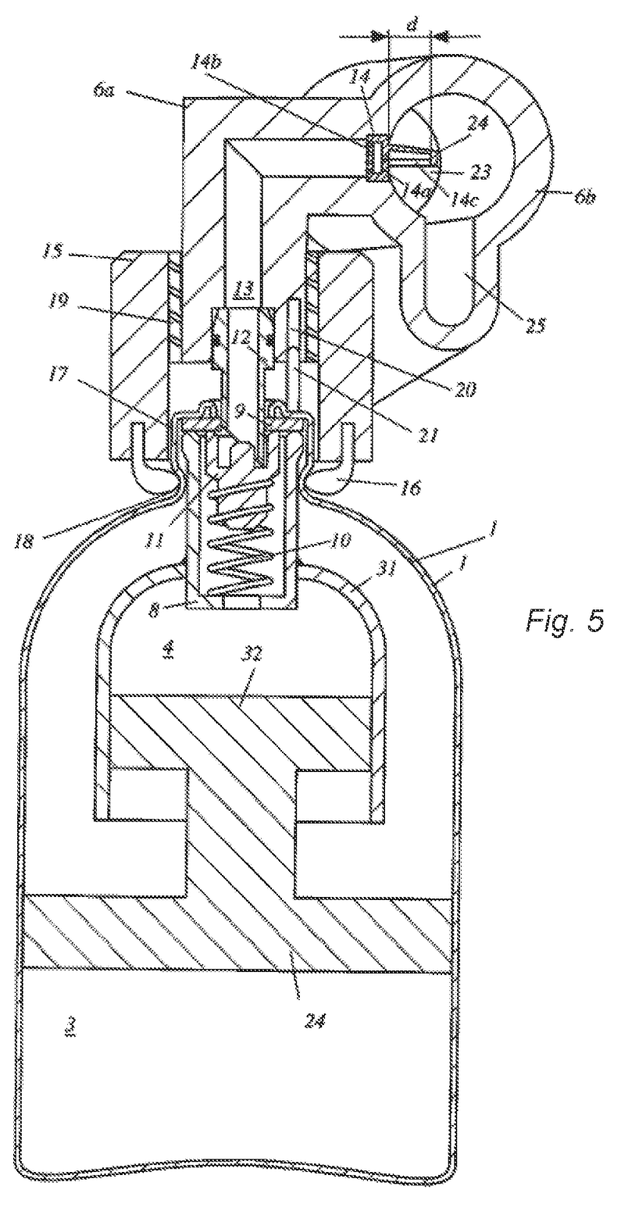
FIG. 5 is the cross-sectional view of an inhaler according to the invention similar to FIG. 1, but wherein a transmission which applies a pressure on the liquid compartment that is higher than that of the gas compartment is provided.

In the inhaler shown in FIG. 5, the atomizer/applicator unit 6a, 6b is constructed as in FIG. 1a. Here the liquid compartment 4 is defined by an inner housing 31 and a liquid piston 32 rigidly connected to the gas piston 24. The unit made up of a gas piston 24 and a liquid piston 32 can be displaced in order to eject inhalation liquid.

Because the liquid piston 32 surface closing the liquid compartment 4 has only approximately half the surface area as the gas piston 24 surface closing the gas compartment 3, the result is a transmission ratio of approximately 2, i.e. the liquid pressure in the liquid compartment 4 is approximately double that of the gas pressure in gas compartment 3 at the same time.

Immediately before the liquid piston 32 reaches its final position by successfully ejecting the maximally ejectable quantity of inhalation liquid, a residual pressure defined ahead of time by design is present in the liquid compartment 4, for example 13 bar (1.3 MPa).

Figure 6:
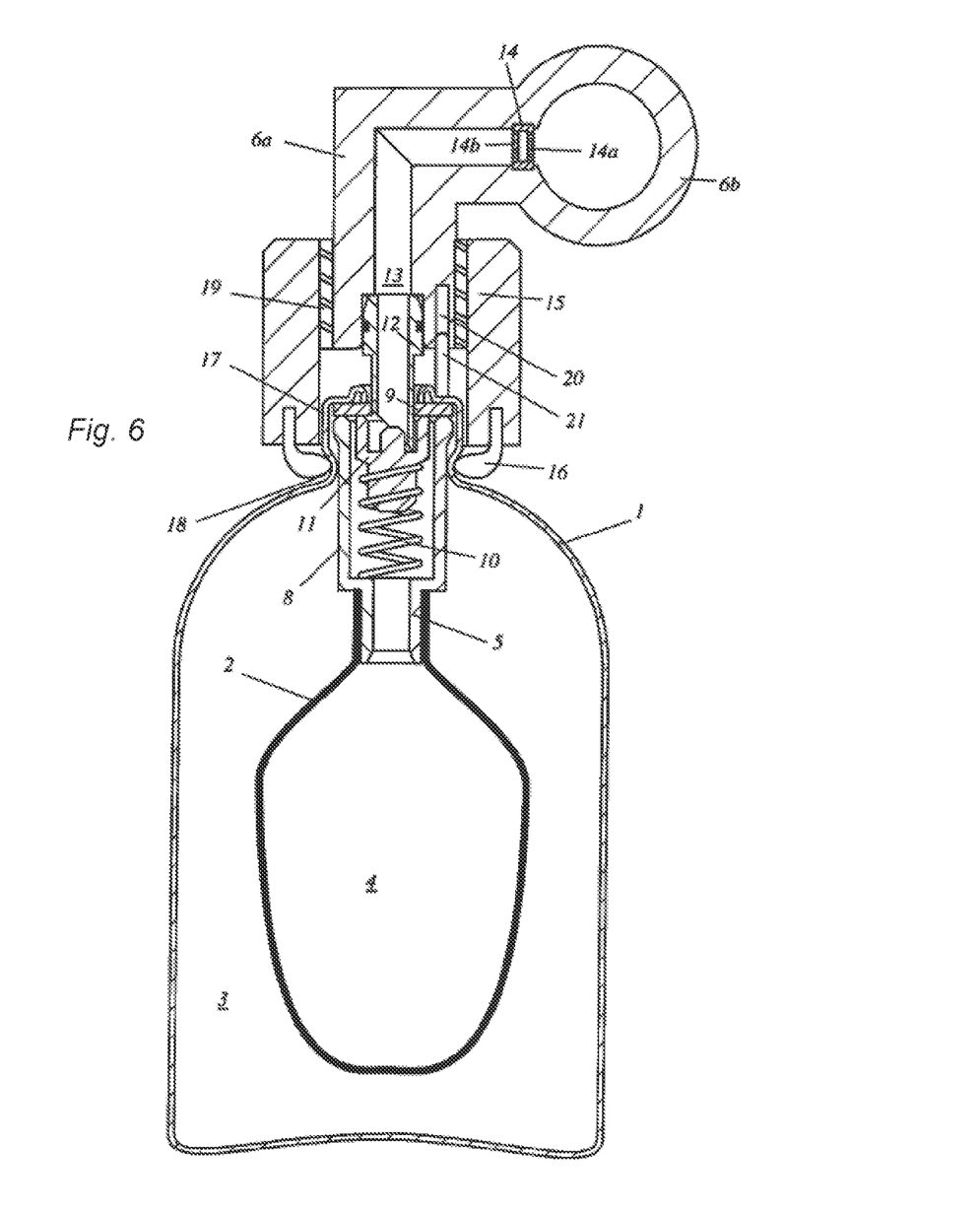
FIG. 6 is the cross-sectional view of an alternative inhaler having a bag-shaped liquid compartment.

The inhaler shown in FIG. 6 has a pressure tank 1 which is divided by the flexible bag 2 into the gas compartment 3 filled with compressed gas and the liquid compartment 4 containing the inhalation liquid. The bag 2 is connected, for example welded or glued, to the inlet connection 5 of the atomizer/applicator unit 6a, 6b (an alternative to the principle shown in FIG. 1).

The valve of the atomizer 6a is similar to conventional valves and has a valve housing 8 which is sealed by the sealing ring 9 made of an elastomer such as rubber or silicone rubber. The spring 10 inserted into the valve housing presses the sealing capsule 11 against the sealing ring 9. By compressing the hollow plunger 12 and pressure vessel 1 relative to one another, the hollow plunger 12, which is beveled at the bottom, pushes the sealing capsule 11 downward in such a way that inhalation liquid can enter the supply channel 13 of the nozzle unit 14 through the valve housing 8 and hollow plunger 12.

The atomizer/applicator unit 6a, 6b is held on the pressure tank 1 by means of a ring 15 having latching lugs 16 evenly distributed around the circumference of the ring. The latching lugs 16 engage in a circumferential constriction 18 of the pressure vessel below the collar 17. The ring 15 is rotatably connected via the thread 19 to the wall of the supply channel 13 seated on the hollow plunger 12. As a result of the pin 21, which engages displaceably in the blind hole 20 of the wall of the supply channel 13 and is welded to the pressure tank 1, the wall of the supply channel 13 and thus the applicator 6b firmly connected to the wall is non-rotatable relative to the pressure tank 1. By rotating the ring 15, the wall of the supply channel 13 can be moved up and down together with the hollow plunger 12 in a controlled manner, thus causing the hollow plunger 12 and pressure vessel 1 to be pressed together relative to one another.

The inhalation liquid is atomized into the interior of the applicator 6b through the nozzle openings of the nozzle body 14 closing the supply channel 13. As in FIG. 1b, the applicator 6b can be designed as a tube, the open end of which is enclosed by the mouth of the user for inhalation.

By means of selective laser exposure and subsequent etching of the exposed regions (selective laser-induced etching), a nozzle plate 14a having a plurality of outlet openings is formed in the nozzle body 14 made of quartz glass with a cylindrical basic shape, in addition to a screen body 14b having a plurality of screen openings, the diameter of which corresponds approximately to the diameter of the outlet openings, in order to keep blockages away from said outlet openings.

The nozzle body 14 can be cast into a one-piece plastics cast part comprising the wall of the supply channel 13 and the applicator 6b, but said nozzle body can also be glued or clamped between two components if the wall of the supply channel 13 and the applicator 6b are not made together as one piece.

If the bag 2 has completely collapsed due to the successful ejection of the maximally ejectable quantity of inhalation liquid, the gas in the gas compartment 3, which then has its maximum volume, has a residual pressure defined in advance by design, for example 13 bar (1.3 MPa).

Figure 7:
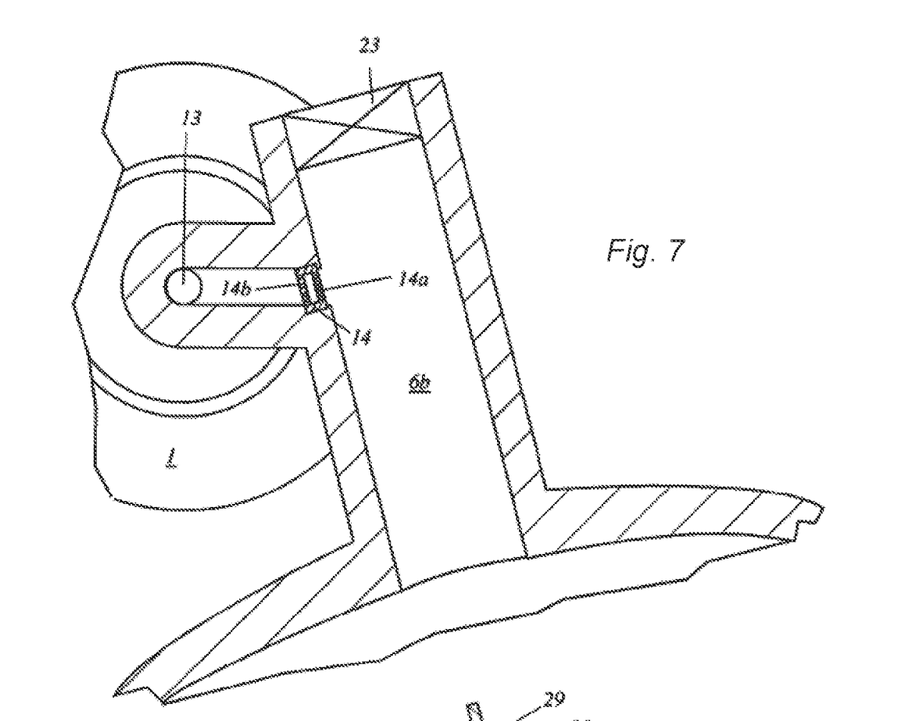
FIG. 7 is a detailed cross-sectional view similar to FIG. 2, but wherein an alternative atomizer having several nozzle openings is provided.

FIG. 7 shows, in a broken perspective view similar to FIG. 2, an inhaler similar to FIG. 6, but with an applicator 6b designed as a mask. The mask can be placed over the mouth and nose of the user for inhalation and is preferably wholly or partially made of a flexible plastics or silicone material.

Figure 8:
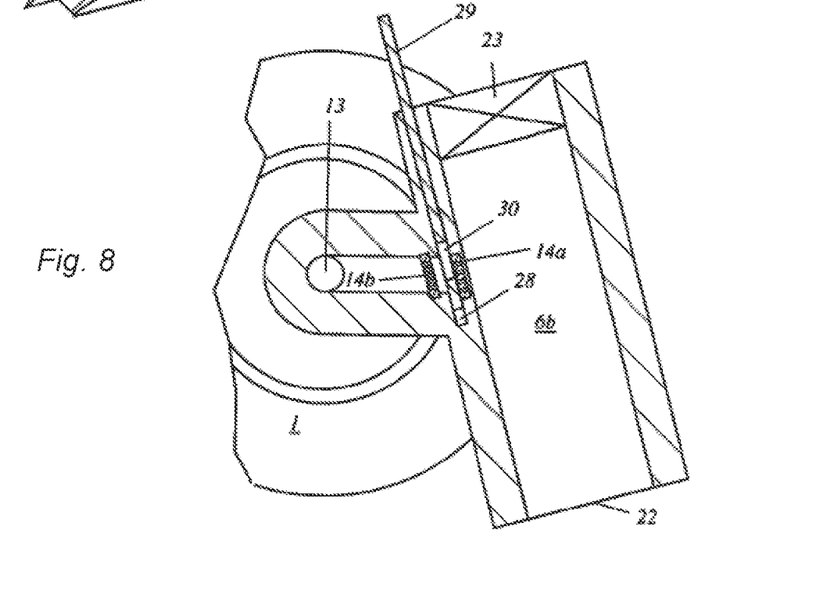
FIG. 8 is a detailed cross-sectional view similar to FIG. 1b, but wherein an alternative atomizer having several nozzle openings and additionally a slider for the variable covering of a part of the nozzle openings is provided.

FIG. 8 shows, in a broken perspective view, an inhaler similar to FIG. 6. However, here the nozzle plate 14a and the screen body 14b are designed as separate components, which are separately cast, glued or otherwise inserted into the unit consisting of the wall of the supply channel 13 and the applicator 6b. Here, too, the nozzle plate 14a and the screen body 14b can be manufactured from quartz glass by means of selective laser-induced etching, but as a result of the simpler design, other manufacturing methods are also possible, such as drilling by means of (especially femtosecond) lasers, lithographic manufacturing, etc.

Furthermore, a slider 29 which can be displaced in a sealed gap 28 is provided here. Depending on the positioning of the slide aperture 30, some of the nozzle openings in the nozzle plate 14a are covered. On the one hand, the volume flow of emerging inhalation liquid can be controlled in this way. On the other hand, the droplet size distribution can be changed if the nozzle openings are of different sizes and are arranged in such a way that, depending on the position of the slider 29 or the position of the slider aperture 30, nozzle openings of different sizes are covered or exposed.

FIG. 9 again shows an alternative inhaler in a cross-sectional view similar to FIG. 6. The inhaler shown in turn has a pressure vessel 1, which is divided by the movable piston 24 into the gas compartment 3 filled with compressed gas and the liquid compartment 4 containing the inhalation liquid. The liquid compartment 4 is connected to the valve housing 5 of the atomizer/applicator unit 6*a*, 6*b*, which has a conical valve seat 25.

Raising the hollow plunger 12 relative to the pressure vessel 1 creates a gap between the conical end of the hollow plunger 12 and the valve seat 25 such that inhalation liquid can enter the supply channel 13 of the nozzle unit 14 through the valve housing 8 and hollow plunger 12.

Figure 9:
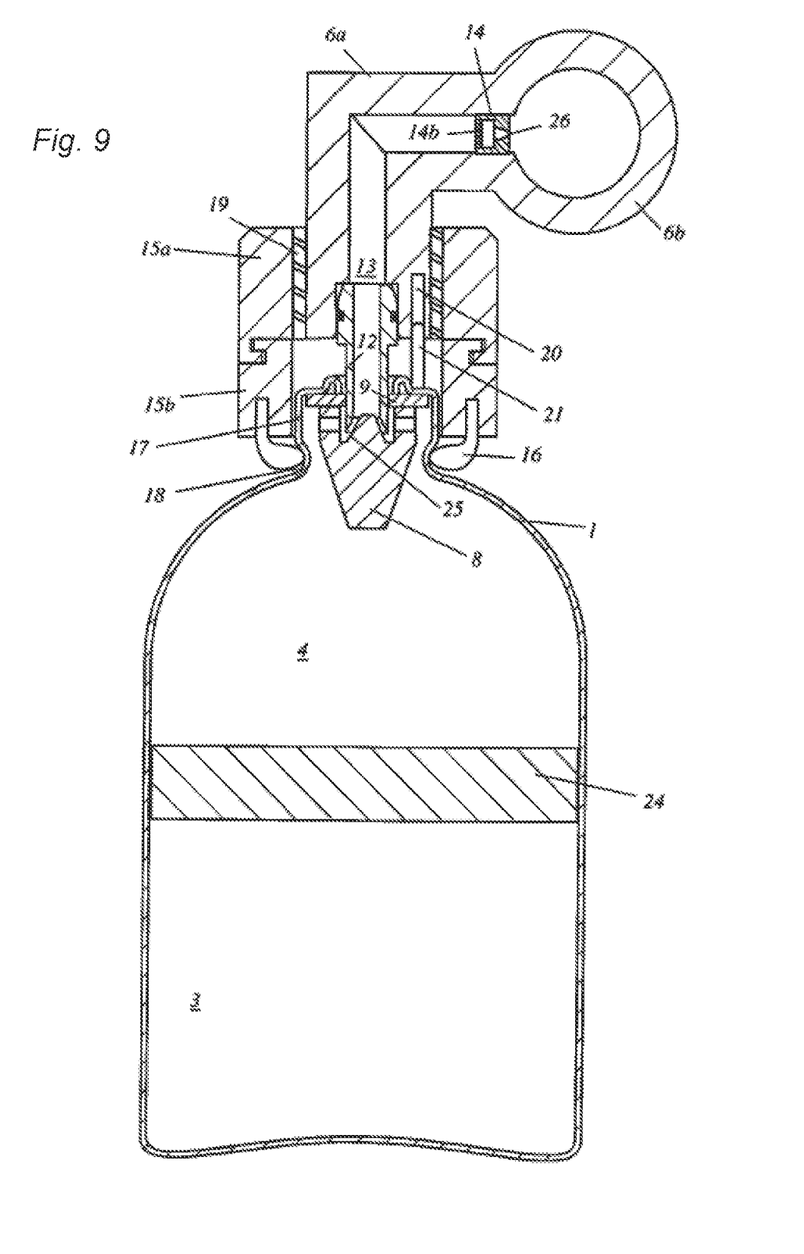
FIG. 9 is the cross-sectional view of an alternative inhaler similar to FIG. 6, but wherein the liquid compartment is separated from the gas compartment by means of a movable piston.

The atomizer/applicator unit 6a, 6b is held on the pressure tank 1 by means of a two-part ring 15a, 15b having latching lugs 16 evenly distributed around the circumference of the lower part 15b of the ring 15a, 15b. The latching lugs 16 engage in a circumferential constriction 18 of the pressure tank 1 below the collar 17. The upper part 15a of the ring 15a, 15b is rotatably connected via the thread 19 to the wall of the supply channel 13 seated on the hollow plunger 12. As a result of the pin 21, which engages displaceably in the blind hole 20 of the wall of the supply channel 13 and is welded to the pressure vessel 1, the wall of the supply channel 13 and thus the applicator 6b firmly connected to the wall is non-rotatable relative to the pressure vessel 1. By rotating the upper part 15a of the ring 15a, 15b, the wall of the supply channel 13 can be moved up and down together with the hollow plunger 12 in a controlled manner, and thus the valve on the valve seat 25 can be opened and closed in a controlled manner.

By adjusting the valve gap between the valve seat 25 and the matching conical counter surface at the lower end of the hollow plunger 12 by rotating the upper part 15a of the ring 15a, 15b, the volume flow of emerging inhalation liquid can be regulated.

The inhalation liquid is atomized into the interior of the applicator 6b through the nozzle opening 26 of the nozzle body 14 closing the supply channel 13. The applicator 6b can again be designed as a tube, as in FIG. 8, the open end of which is enclosed by the mouth of the user for inhalation.

By means of selective laser exposure and subsequent etching of the exposed areas (selective laser-induced etching), a cylindrical-conical cavity 27 is formed in the nozzle body 14 made of quartz glass with a cylindrical basic shape. On the inlet side, the nozzle body has a screen body 14b having a plurality of screen openings, the diameter of which corresponds approximately to the diameter of the outlet opening 26, in order to keep blockages from said outlet openings. The nozzle body 14 can be cast as a one-piece plastics cast part comprising the wall of the supply channel 13 and the applicator 6b, but said nozzle body can also be glued or clamped between two components if the wall of the supply channel 13 and the applicator 6b are not made as one piece together.

If the piston 24 has reached its final position by successfully ejecting the maximally ejectable quantity of inhalation liquid, the gas in the gas compartment 3, which then has its maximum volume, has a residual pressure defined in advance by design, for example 13 bar (1.3 MPa).

The invention claimed is:

1. A portable device for administering a physiologically active liquid, comprising:
   a container for holding the liquid;
   pressurizing means for applying pressure to the liquid;
   an atomizer for atomizing the liquid; and
   an applicator for administering atomized liquid,
   wherein the atomizer comprises:
      at least one Rayleigh nozzle through which the liquid is ejected from the container, and
      an impact element, wherein the atomizer is configured such that, in a pressure range generated with the pressurizing means, a liquid jet emerging from the at least one Rayleigh nozzle breaks up, under a free break up regime, into almost monodisperse droplets prior to striking the impact element, the impact element on a nozzle outlet side for impact atomization to atomize the droplets from the liquid jet, the impact element being functionally combined with the at least one Rayleigh nozzle.

2. The portable device according to claim 1, further comprising a collection device for collecting excess liquid dripping or running from the impact element.

3. The portable device according to claim 2, wherein the collection device and the applicator are integrated into a common component.

4. The portable device according to claim 2, wherein the collection device and the impact element are integrated into a common component.

5. The portable device according to claim 2, wherein the collection device comprises a collection reservoir.

6. The portable device according to claim 5, wherein the collection reservoir comprises an absorbent material.

7. The portable device according to claim 2, wherein the portable device is configured to supply at least part of the excess liquid to the atomizer for re-atomizing.

8. The portable device according to claim 1, wherein the container is a pressure tank having a gas compartment filled with compressed gas and a liquid compartment filled with the liquid,
   wherein the atomizer has a valve such that the liquid is ejected from the liquid compartment through the at least one Rayleigh nozzle when the valve is open, in that the gas compartment increases proportionally to the quantity of liquid ejected by expansion of the compressed gas and the liquid compartment thereby decreases by the volume of the liquid ejected, such that a maximum possible change in volume of the gas compartment or the liquid compartment compared to an initial filling state of the gas compartment or the liquid compartment, respectively, defines a maximum ejection quantity of the liquid for the initial filling state.

9. The portable device according to claim 8, wherein the valve is configured as a regulating valve configured to regulate a volume flow of the liquid being ejected.

10. The portable device according to claim 8, wherein the pressure of the compressed gas in the initial filling state is such that the pressure in the liquid compartment does not fall below 13 bar (1.3 MPa) until the maximum ejection quantity of the liquid has been successfully ejected.

11. The portable device according to claim 8, wherein the pressure of the compressed gas in the initial filling state is at least 18 bar (1.8 MPa).

12. The portable device according to claim 8, further comprising a transmission which increases the pressure in the liquid compartment compared to the pressure in the gas compartment.

13. The portable device according to claim 12, wherein the transmission has a gas piston delimiting the gas compartment on one side with a gas compartment piston surface on a gas compartment side and a liquid piston delimiting the liquid compartment on one side with a liquid compartment piston surface on a liquid compartment side,
   wherein a surface area of the liquid compartment piston surface is smaller than a surface area of the gas compartment piston surface.

14. The portable device according to claim 13, wherein the surface area of the liquid compartment piston surface is smaller than or equal to half the surface area of the gas compartment piston surface.

15. The portable device according to claim 1, wherein the pressurizing means comprises a hand pump or an electrically operated pump.

16. The portable device according to claim 1, wherein the pressurizing means comprises a spring system.

17. The portable device according to claim 1, wherein the at least one Rayleigh nozzle is manufactured lithographically.

18. The portable device according to claim 1, wherein the at least one Rayleigh nozzle is manufactured by sintering ceramic or plastics.

19. The portable device according to claim 1, wherein the at least one Rayleigh nozzle is manufactured by electroerosion.

20. The portable device according to claim 1, wherein the at least one Rayleigh nozzle is manufactured by laser action.

21. The portable device according to claim 1, wherein the portable device is an inhalation device, the liquid is an inhalation liquid, and the applicator comprises at least one of a mouthpiece, a mouth mask, or a nose mask.

22. The portable device according to claim 21, wherein the applicator has the mouthpiece and the inhalation liquid contains nicotine.

23. The portable device according to claim 1, wherein the portable device is an ophthalmic nebulizer and the applicator comprises an eye mask.

24. The portable device according to claim 1, wherein a screen arrangement is arranged upstream to the at least one Rayleigh nozzle on a nozzle inlet side.

25. The portable device according to claim 1, wherein the atomizer comprises multiple Rayleigh nozzles which includes the at least one Rayleigh nozzle, wherein the multiple Rayleigh nozzles are excludable from a supply of the liquid individually or in groups.

* * * * *